Figure 1:
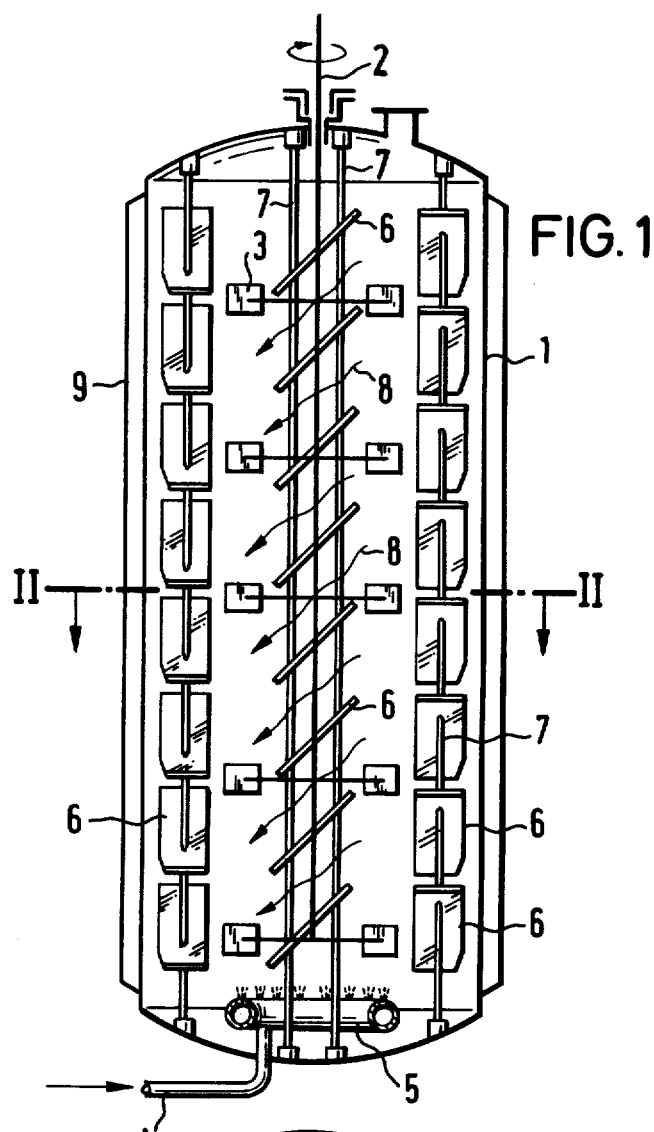

United States Patent [19]

Heine et al.

[11] 4,378,436

[45] Mar. 29, 1983

[54] PROCESS AND DEVICE FOR IMPROVING THE QUALITY OF MIXING OF LIQUID ESPECIALLY VISCOUS MEDIA

[75] Inventors: Helmut Heine, Kronberg; Karl Kühn, Kelkheim; Wolfgang Sittig, Hofheim am Taunus, all of Fed. Rep. of Germany

[73] Assignee: Hoechst Aktiengesellschaft, Frankfurt am Main, Fed. Rep. of Germany

[21] Appl. No.: 261,195

[22] PCT Filed: Sep. 5, 1980

[86] PCT No.: PCT/EP80/00093

§ 371 Date: May 8, 1981

§ 102(e) Date: Mar. 26, 1981

[87] PCT Pub. No.: WO81/00722

PCT Pub. Date: Mar. 19, 1981

[30] Foreign Application Priority Data

Sep. 8, 1979 [DE] Fed. Rep. of Germany ....... 2936388

[51] Int. Cl.³ .............. C12N 1/00; C12M 1/04; C12M 1/06; C12M 1/08
[52] U.S. Cl. ..................... 435/243; 261/93; 261/123; 435/313; 435/314; 435/315; 435/316
[58] Field of Search ............. 261/87, 93, 123; 435/313, 314, 315, 316, 243

[56] References Cited

U.S. PATENT DOCUMENTS

| 1,585,169 | 5/1926 | Perkins et al. | 366/303 |
|---|---|---|---|
| 2,085,947 | 7/1937 | Booth | 261/93 |
| 2,453,592 | 11/1948 | Putney | 422/227 X |
| 2,530,814 | 11/1950 | De Becze et al. | 435/315 X |
| 2,767,965 | 10/1956 | Daman | 261/87 |
| 2,973,095 | 2/1961 | Anderson et al. | 261/87 X |
| 3,092,678 | 6/1963 | Braun | 261/87 X |
| 3,378,141 | 4/1968 | Warman | 261/87 X |
| 3,460,810 | 8/1969 | Mueller | 261/93 X |
| 3,572,661 | 3/1971 | Muller | 261/93 X |
| 3,752,742 | 8/1973 | Jackel et al. | 435/315 X |
| 3,882,016 | 5/1975 | Green | 261/87 X |
| 4,001,090 | 1/1977 | Kalina | 435/243 |
| 4,019,962 | 4/1977 | Allen et al. | 435/315 |

FOREIGN PATENT DOCUMENTS

| 175862 | 8/1963 | Austria . |
| 743984 | 11/1943 | Fed. Rep. of Germany . |
| 753388 | 7/1978 | Fed. Rep. of Germany . |
| 1523664 | 3/1968 | France . |
| 1546174 | 11/1968 | France . |
| 1571532 | 6/1969 | France . |
| 2041779 | 2/1971 | France . |
| 2273062 | 12/1975 | France . |
| 2320984 | 3/1977 | France . |
| 478354 | 1/1938 | United Kingdom . |
| 1178017 | 1/1970 | United Kingdom . |
| 1223418 | 2/1971 | United Kingdom . |

*Primary Examiner*—Robert J. Warden
*Attorney, Agent, or Firm*—Curtis, Morris & Safford

[57] ABSTRACT

The invention relates to a process for improving the quality of mixing of liquid especially viscous media in stirred tank reactors, wherein a change in direction of the medium set in motion is brought about at one point or at several points of the inner wall of the reactor at different levels, in a direction vertical to the angle of approaching flow (attack). The process is especially suitable for fermentation reactions.

The invention moreover relates to a corresponding stirred tank reactor.

11 Claims, 2 Drawing Figures

PROCESS AND DEVICE FOR IMPROVING THE QUALITY OF MIXING OF LIQUID ESPECIALLY VISCOUS MEDIA

To perform reactions in the liquid phase, it is necessary to convey the reactants required to the zone where the reaction takes place by mixing and/or stirring, followed by removal of the reaction products. The transport paths in the case of catalytic reactions are determined by the distribution of the catalytically active substances and in the case of fermentations by the distribution of the cells.

It is known to carry out reactions of the above type in stirred tanks. Particularly with highly viscous and non-Newtonian or intrinsically viscous reaction mixtures dead zones are formed in those areas which are only slightly stirred which due to disintegration phenomena, no longer participate in the supply and removal of matter. With chemical reactions this may lead to so-called temperature nests since the heat generated by the reaction is not dissipated, or to a breakdown of the reaction caused by self-locking as a result of over-concentrations. In the case of fermentation reactions, this formation of dead zones influences the desired metabolic reactions, which may even result in irreversible damage and destruction of the cells. In the case of batch fermentation of antibiotics of up to 300 hours, nearly all cells remain occasionally in such zones, even if the latter represent only 2 to 3% of the volume of the reactor.

The stirring means serves to mix the reaction system, to divide and disperse the injected gas, to dissipate the reaction heat via the reactor jacket and/or via cooling inserts and under certain circumstances to prevent the formation of agglomerates beyond a certain size due to shearing forces acting on the reaction system. Especially when used in fermentation reactors, these agitator means have been optimized mainly with a view to the quality of the mass transfer from the gas phase into the liquid phase attributable thereto and not so much with a view to the quality of their mixing effect. The agitator efficiency has been improved and the volumes of the reactor have been increased, while the efficiency of the biological cell cultures increased, and the reactors, the contents of which were considered as homogeneously mixed, have been divided into aeration, degassing and heat exchange zones.

The nutrient solutions in actual use exhibit a non-Newtonian intrinsically viscous behavior. The stirrers used have in most cases three to five levels and the ratio of diameter of the stirrer to diameter of the tank is from 0.35 to 0.65. To prevent rotation of the contents of the reactor at the same speed as the stirrer, are used wherein deflectors are mounted close to the wall wherein the width of the deflectors in vertical orientation to the angle of approaching flow is about 8 to 10% of the diameter of the vessel. Especially in the case of intrinsically viscous reaction mixtures stationary pockets of turbulences or even dead zones having the above-described disadvantages are formed behind these deflectors.

It is an objective of the present invention to overcome the disadvantages of the present state of the art and particularly to control the flow direction in such a way that the above-described dead zones do not occur, the mixing effect of the stirrer means and the heat transfer are improved and rotational movement of the reaction mixture in the reactor with little mixing effect is prevented.

The present invention therefore relates to a process for improving the quality of mixing of liquid, in particular viscous media in stirred tank reactors, which comprises changing the direction of the medium set in motion by stirring means, at one or several locations along the internal wall of the reactor and at different levels, in a direction vertical to the angle of approaching flow.

The present invention moreover relates to a stirred tank reactor provided with the usual stirrer means, with elements acting on the flow, i.e., deflectors, optionally with further inserts, with jacket cooling elements and with aerating means, wherein the deflectors are baffle elements that are arranged at one or several points along the periphery of the reactor at different levels, which elements cause a change in direction of the flow in a direction vertical to the angle of approaching flow.

All liquid systems such as gassed suspensions, emulsions and/or dispersions can be used in the process according to the invention. The process of the present invention is particularly suitable for gassed fermentation broths.

The advantages of the process of the invention are particularly evident in the case of viscous, especially non-Newtonian, intrinsically viscous, liquid systems wherein the viscosity is above 400 cP and particularly of from 1,000 to 5,000 cP.

Examples of suitable liquid systems which can be used in the present invention include tylose solutions, starch solutions, polymerization mixtures, fermentation broths for preparing antibiotics such as penicillin, tetracycline, cephalosporin, streptomycin, xanthan fermentations and so on.

The flow of liquid caused to move by the stirring means radially and tangentially with respect to the reactor wall are deflected according to the invention in a vertical direction with regard to the angle of approaching flow, that is in the direction of the longitudinal axis of the reactor or the axis of the stirring means. Deflection in most cases takes place in one direction only, namely upward or downward. Under certain circumstances it may be advantageous to deflect alternately downward and upward. The deflection force depends on the angle of inclination of the individual baffle elements of the deflector(s), on the viscosity of the liquid medium and on the stirring energy. In accordance with the present invention, as a result of the change in direction of the flowing medium the motion of the mixture is increased in a defined preferential direction in the zones close to the reactor wall, while the speed of the flowing medium is increased.

The stirred tank reactor according to the invention may theoretically have any shape. Generally, however, a vertical cylinder is used.

The deflector elements arranged in the reactor according to the present invention consist of a number of thin flat elements, preferably plates, which are mounted in the direction of the longitudinal axis of the reactor. Preferably they are arranged in a vertical direction with one above the other and inclined towards the angle of approaching flow, i.e., to a level vertical to the longitudinal axis of the reactor or of the stirrer. This inclination angle decreases as the viscosity of the medium decreases and the speed of the approaching flow increases. This angle is suitably from ±20° to ±85°, preferably from ±30° to ±60°. Generally this angle is identical for all elements of one deflection unit. If there are several deflection units in the reactor, they may have different angles of approaching flow, especially alternating angles of approaching flow. In the latter case the flow is deflected alternately in one direction (upward) and then in the opposite direction (downward).

The plate-shaped baffle elements of the deflector according to the invention are in most cases of rectangular or quadrangular structure. They may be of flat or curved construction. In special cases these plate-shaped elements may consist of close-meshed nets, provided that they withstand the pressure of the approaching flow. The dimension of the baffle elements is in most cases such that the distance to the wall of the reactor is of from 0.01 to 0.1 D(D=diameter of the reactor), preferably 0.01. Furthermore they extend in a radial direction and preferably over 8 to 20% of the diameter of the reactor.

Generally the baffle elements are arranged one above the other deflection unit and may be fixed directly to the inner wall of the vessel. Preferably, however, they are mounted on adequate holding means consisting for example of one or two rods which extend in the longitudinal direction of the reactor, in a manner such that the angle of approaching flow may be adjusted in variable manner. The distance of the individual baffle elements from one another is preferably from 3 to 30, preferably 10 to 15, % of the diameter of the reactor. The number of the individual elements in one deflector unit depends on the height of the vessel.

Generally from 2 to 20 individual elements per meter of reactor height will be sufficient.

The number of the deflection units according to the invention is preferably from 1 to 8, preferably 4.

In a further embodiment of the invention the deflection units that is the holding means and the individual baffle elements, may be hollow to permit the introduction of a cooling or heating medium.

As stirring means according to the present invention there may be used generally all means known for this purpose which ensure adequate flow characteristics and a satisfactory stirrer efficiency, for example impeller mixers, turbine mixes, pitched flat blade impellers, flat blade mixers, inter-multiblade countercurrent impeller, multiblade countercurrent impeller, self aspiring stirrer and so on. Stirring means of the above type which are suitable for the purpose of the present invention are described, for example, in the article of Kipke titled "Rühren von dünnflüssigen and mittelviskosen Medien", CIT 51 (1979), pages 430–436 or in the article of Sitting and Heine titled "Erfahrungen mit grosstechnischen eingesetzten Bioreaktoren", CIT 49 (1977), Nr. 8, pages 595–605. Preferably there are used in accordance with the present invention multi-level blade stirrers or multi-level disk stirrers, with a distance between the individual levels of from 1 to 3 times the stirrer diameter. The number of the blades per propeller is generally from 3 to 6 and the ratio of diameter of stirrer to diameter of reactor is in most cases from 0.35 to 0.65.

The stirred tank reactor according to the present invention moreover contains the usual inserts, for example funnel tubes, valves, pumps, tubes, control and measuring instruments and optionally additional means such as reflux condensers.

When the stirred tank reactor is used for fermentation purposes, it is provided with the usual means for gassing the reaction medium, i.e. corresponding inlets and outlets and a tubular nozzle generally connected with the inlet; alternatively single nozzle or an air jet belt may be used. In the case of highly endothermic or exothermic reactions the reactor is moreover provided with a double jacket ensuring an adequate jacket cooling.

Figure 2:
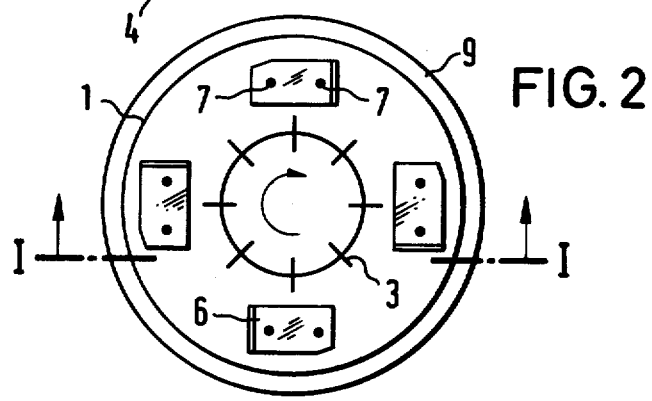

The process and the device according to the present invention will be illustrated in the accompanying drawings wherein FIG. 1 represents a lateral sectional view of the reactor along line I—I of FIG. 2, and FIG. 2 represents a cross-sectional top view along line II—II of FIG. 1.

In FIG. 1 numeral (1) represents the reactor shaped as a vertical cylinder, (2) represents the multi-level blade stirrer provided with blades (3). The reaction gas is injected into the reactor via inlet (4) through jet belt (5), aspirated by the stirrer together with the fluid reaction suspension and moved radially and tangentially in the direction of the reactor wall, where the flow is deflected downward along the flow lines (8) by the deflection unit according to the invention, which consists of individual elements (6) and holding means (7) consisting of two rods. This brings about a defined preferential direction of the movement of the mixture and simultaneously a higher speed of the mixture in the zones close to the wall, as a result of which the heat transfer to cooling jacket (9) is also improved.

EXAMPLE 1

A 1.3% tylose solution was mixed in a 130 liter stirred tank equipped with four deflection units according to the invention each of which consisting of 8 rectangular baffle plates of 0.0032 $m^2$ surface area each and with one two-level blade stirrer (number of blades: 6). The mixing time was determined by measurements of the color change. The angle of approaching flow of the baffle elements of the deflection units according to the invention was 45°. The baffle plates were mounted on two rods fixed to the bottom and to the top of the reactor and extended in radial direction over 10% of the diameter of the reactor at a distance to the reactor wall of about 0.01 D.

With a mechanical power input (stirrer energy) of 5 $kW/m^3$ the mixing time was 12 seconds.

COMPARATIVE TEST

When using four conventional deflector units of 45 mm width that are arranged vertically with regard to the angle of approaching flow the mixing time was found to be 20 seconds.

EXAMPLE 2

Example 1 was repeated using, however, a flat blade stirrer instead of a two-level disk stirrer. With a power input (stirring energy) of about 1 $kW/m^3$ the mixing time was found to be 18 seconds.

COMPARATIVE TEST

When using conventional deflectors under the conditions of Example 2 the mixing time was 50 seconds.

EXAMPLE 3

Penicillin was prepared in a fermentation vessel of 40 $m^3$ volume equipped with four deflection units according to the invention each consisting of 18 rectangular baffle plates of 0.075 $m^2$ surface area each. The baffle plates extended in radial direction over 9% of the diameter of the vessel and at a distance of the wall of about 0.15 D. The angle of approaching flow was about 40°. Three turbine impellers were used for stirring and gassing was effected by a device as shown in FIG. 1.

26 m³ of drinking water were placed in this fermentation vessel and the following raw materials were added thereto:

1,320 kg of soybean flour,
250 kg of sodium thiosulfate,
230 kg of calcium carbonate,
165 kg of soybean oil,
3,300 kg of lactose and
150 kg of phenoxyacetic acid.

The pH of the resulting suspension was adjusted to 6.0 with a sodium hydroxide solution and sterilization was brought about by steaming at 120° C. for 40 minutes. After cooling of the nutrient solution to 25° C., the fermentation vessel was inoculated with 3000 liters of a well washed inoculum of penicillin. The contents of the vessel were subjected to fermentation at 25° C. while aerating with 0.5 liter of air per liter of liquid volume with a stirring energy of from 2.5 to 3 kW/m³. Soybean oil was added during the fermentation process in several portions of about 5 liters in a total quantity of from 5 to 1,000 liters to defoam the fermentation mixture. The fermentation time was 150 hours and the yield was 14,950 U/ml.

COMPARATIVE TEST

Example 3 was repeated using, however, a fermentation vessel equipped with conventional deflection units of 0.1 D width each instead of the four deflection units according to the invention.

The yield was found to be about 13,500 U/ml.

EXAMPLE 4

Into the fermentation vessel according to Example 3 there were introduced 22 m³ of drinking water, whereto the following raw materials were added:

1,100 kg of peanut flour,
1,250 kg of crystal sugar,
143 kg of ammonium sulfate,
310 kg of calcium carbonate,
25 kg of citric acid,
65 kg of lard,
20 kg of $Na_2HPO_4.12H_2O$,
19 kg of $MgSO_4.7H_2O$,
2.5 kg of $MnSO_4.1H_2O$,
5.0 kg of $ZnSO_4.7H_2O$,
0.310 kg of $FeSO_4.7H_2O$ and
0.310 kg of $Al_2(SO_4)_3.18H_2O$.

The nutrient solution was sterilized with direct steam at 120° C. for 30 minutes, cooled to a temperature of 28° C. and inoculated with 1,500 liters of well washed tetracycline inoculum. Fermentation was carried out at 28° C. up to the twelfth hour and was carried to completion at 25° C. Aeration was effected with 0.5 liter of air per liter of liquid volume. The stirring energy was 2 kW/m³. After about 48 hours there was added a solution of 750 kg of sugar and 180 kg of ammonium sulfate in 2,000 liters of drinking water which had been sterilized at 120° C. for 30 minutes. A second portion consisting of 750 kg of sugar in 2,000 liters of drinking water that had been sterilized as specified above was added after about 72 hours.

To defoam the fermentation mixture there was added during the fermentation lard oil and soybean oil, depending on the foaming behavior. The final volume was found to be about 32 m². Fermentation was complete after 160 hours.

The yield was about 9,359 U/ml.

COMPARATIVE TEST

Example 4 was repeated using, however, a fermentation vessel equipped with 4 conventional deflection units each having 0.1 D width. The yield was about 8,300 U/ml.

We claim:

1. A reaction vessel for intimate and homogeneous mixing of liquid viscous media which comprises, in combination, a mixing vessel having a mixing chamber, inlet and outlet means for charging gas and liquid viscous media to said vessel, mixing means for effecting liquid media flow, aeration means, cooling means comprising a cooling jacket cooperating with the exterior wall of said mixing vessel and flow deflector means comprising holding means for positioning one or more deflector units each unit having a plurality of baffle elements located at one or more points along the periphery of the vessel at a distance from the vessel wall equal to 1% to 10% of the vessel diameter and located at a plurality of points along the longitudinal axis of the vessel and separated from each other along said longitudinal axis at a distance equal to 3% to 30% of the vessel diameter, said baffle elements being positioned towards the direction of approaching liquid media flow such that said direction of flow is controllably varied along a defined path which is vertical to said direction of approaching flow.

2. The reaction vessel of claim 1 containing from 1 to 8 deflector units.

3. The reaction vessel of claim 1 wherein said baffle element is positioned to form an angle between ±20° to ±85° with respect to the direction of approaching liquid media flow whereby said angle decreases with decreasing viscosity of the liquid viscous media.

4. The reaction vessel of claim 1 wherein said baffle elements have a a quadrangular or rectangular plate shape.

5. The reaction vessel of claim 1 wherein the baffle elements of at least one deflector unit are affixed to the vessel wall.

6. The reaction vessel of claim 1 wherein said holding means consists of one or more rods extending along the longitudinal axis of said vessel and positioned to controllably vary the direction of approaching liquid media flow.

7. The reaction vessel of claim 6 wherein said rods and deflector units are hollow and adapted to receive heating or cooling medium.

8. The reaction vessel of claim 1 having 2 to 20 baffle elements per meter of vessel height.

9. The reaction vessel of claim 1 further containing inserts such as flow and temperature measuring devices, valves and tubes.

10. A process for intimate and homogeneous mixing of liquid viscous media in a mixing vessel wherein a liquid viscous media is charged to said vessel, the process comprising stirring said liquid viscous media to effect flow thereof in radial and tangential direction relative to the vessel wall and deflecting said flow in a defined path vertical to the direction of flow effected by stirring said liquid and increasing the flow of said liquid viscous media near the vessel wall by means of one or more deflector units each having a plurality of baffle elements located at one or more points along the periphery of the vessel at a distance from the vessel wall equal to 1% to 10% of the vessel diameter and located at a plurality of points along the longitudinal axis of the vessel and separated from each other along said longitudinal axis at a distance equal to 3% to 30% of the vessel diameter wherein said baffle elements are positioned towards the direction of approaching liquid media flow.

11. The process of claim 10 wherein said liquid viscous media is a fermentation broth.

* * * * *